United States Patent [19]
Ullman et al.

[11] Patent Number: 5,516,641
[45] Date of Patent: May 14, 1996

[54] METHOD FOR DETECTION OF SPECIFIC NUCLEIC ACID SEQUENCES

[75] Inventors: Edwin F. Ullman, Atherton; Thomas C. Goodman; Paul D. Stull, both of Mountain View, all of Calif.

[73] Assignee: Syntex (U.S.A.) Inc., Palo Alto, Calif.

[21] Appl. No.: 401,660

[22] Filed: Mar. 10, 1995

Related U.S. Application Data

[63] Continuation of Ser. No. 200,373, Feb. 18, 1994, which is a continuation of Ser. No. 993,156, Dec. 18, 1992, which is a continuation of Ser. No. 236,967, Aug. 25, 1988, Pat. No. 5,185,243.

[51] Int. Cl.$^6$ .............................. C12Q 1/68; C12P 19/34
[52] U.S. Cl. .................... 435/6; 935/77; 935/78; 435/91.1
[58] Field of Search ................... 435/6; 935/77, 935/78

[56] References Cited

U.S. PATENT DOCUMENTS

| | | |
|---|---|---|
| 4,423,153 | 12/1983 | Ranney et al. . |
| 4,480,040 | 10/1984 | Owens et al. . |
| 4,486,539 | 12/1984 | Ranki et al. . |
| 4,490,472 | 12/1984 | Gottlieb . |
| 4,563,419 | 1/1986 | Ranki et al. . |
| 4,599,303 | 7/1986 | Yabusaki et al. . |
| 4,647,529 | 3/1987 | Rodland et al. . |
| 4,675,283 | 6/1987 | Roninson . |
| 4,677,054 | 6/1987 | White et al. . |
| 4,683,194 | 7/1987 | Saiki et al. . |
| 4,683,195 | 7/1987 | Mullis et al. ............... 435/6 |
| 4,683,202 | 7/1987 | Mullis . |
| 4,716,106 | 12/1987 | Chiswell . |
| 4,725,536 | 2/1988 | Fritsch et al. . |
| 4,731,325 | 3/1988 | Palva et al. . |
| 4,775,619 | 10/1988 | Urdea . |
| 4,851,331 | 7/1989 | Vary et al. . |
| 4,868,104 | 9/1989 | Kurn et al. . |
| 4,883,750 | 11/1989 | Whiteley et al. . |
| 4,994,368 | 2/1991 | Goodman et al. . |

FOREIGN PATENT DOCUMENTS

| | | |
|---|---|---|
| 0198662A1 | 10/1986 | European Pat. Off. . |
| 0198662 | 10/1986 | European Pat. Off. ............. 435/6 |
| 0246864 | 11/1987 | European Pat. Off. ............. 435/6 |
| 0302175A2 | 2/1989 | European Pat. Off. . |
| 2169403 | 7/1986 | United Kingdom ................ 435/6 |

OTHER PUBLICATIONS

Gardner, Biotechniques, vol 1: pp. 38–41, (1983) "Non–radioactive DNA Labeling: Detection of Specific DNA and RNA Sequences on Nitrocellulose and in situ Hybridizations".

Langer, et al., Proc. Natl. Acad. Science USA, vol. 78:11, pp. 6633–6637, (Nov. 1981) "Enzymatic synthesis of biotin–labeled polynucleotides: Novel nucleic acid affinity probes".

Brigati, et al., Virology, vol. 126: pp. 32–50, (1983) "Detection of Viral Genomes in Cultured Cells and Paraffin–Embedded Tissue Sections Using Biotin–Labeled Hybridization Probes".

Lewin, Science, vol. 221, p. 1167 only, (1983) "Genetic Probes Become Ever Sharper".

Bauman, et al., J. Histochem. Cytochem, vol. 29:2, pp. 227–238, (1981) "Cytochemical Hybridization with Fluorochrome–labeled RNA".

Landegren, et al., Science, vol. 241, pp. 1077–1080, (1988) "A Ligase–Mediated Gene Detection Technique".

Goldkorn, et al., Nucleic Acids Research, vol. 14:22, pp. 9171–9191, (1986) "A simple and efficient enzymatic method for covalent attachment of DNA to cellulose".

Bischofberger, et al., Nucleic Acids Research, vol. 15:2, pp. 709–716, (1987) "Cleavage of single stranded oligonucleotides by EcoRI restriction endonuclease".

Wiaderkiewiez, et al., Nucleic Acid Res., vol. 15:19, pp. 7831–7848, (1987) "Mismatch and blunt to protruding–end joining by DNA ligases".

Goffin, et al., Nucleic Acid Res., vol. 15:21, pp. 8755–8771, (1987) "Nicks 3' or 5' to AP sites or to mispaired bases, and one–nucleotide gaps can be sealed by T4 DNA ligase".

Krupp et al., FEBS Letts 212(2):271–275 (Feb. 1987).

*Primary Examiner*—Stephanie W. Zitomer
*Attorney, Agent, or Firm*—Theodore J. Leitereg; Janet K. Kaku; Mark L. Bosse

[57] ABSTRACT

A kit is disclosed for a method for detecting the presence of a target polynucleotide sequence. The kit comprises a first polynucleotide sequence and a second polynucleotide sequence complementary to non-contiguous portions of a target polynucleotide sequence, which first and second sequences are covalently attached when they are hybridized to the target sequence. The presence of the covalently attached first and second sequences is related to the presence of the target polynucleotide sequence. The invention may be applied to target polynucleotide sequences in DNA or RNA. Specific target polynucleotide sequences of interest will frequently be characteristic of particular microorganisms, viruses, viroids, or genetic characteristics, including genetic abnormalities.

2 Claims, No Drawings

METHOD FOR DETECTION OF SPECIFIC NUCLEIC ACID SEQUENCES

This is a file wrapper continuation of U.S. patent application Ser. No. 08/200,373 filed Feb. 18, 1994, which in turn is a file wrapper continuation of U.S. patent application Ser. No. 07/993,156, filed Dec. 18, 1992, which in turn is a continuation of U.S. patent application Ser. No. 07/236,967, filed Aug. 25, 1988, now U.S. Pat. No. 5,185,243.

BACKGROUND OF THE INVENTION

1. Field of the Invention

This invention relates to methods for detecting the presence of target nucleotide sequences.

Nucleic acid hybridization has been employed for investigating the identity of nucleic acids. Hybridization is based on complementary base pairing. When at least partially complementary single stranded nucleic acids are incubated in solution under suitable conditions of temperature, pH and ionic strength, complementary base sequences pair to form double stranded stable hybrid molecules. The ability of single stranded deoxyribonucleic acid (ssDNA) or ribonucleic acid (RNA) to form a hydrogen bonded structure with its complementary nucleic acid sequence has been employed as an analytical tool in recombinant DNA research. The availability of radioactive nucleoside triphosphates of high specific activity and the synthetic methods of incorporating these nucleotides into nucleic acid probes such as the $^{32}P$ labelling of DNA with $T_4$ polynucleotide kinase and other well known methods has made it possible to identify, isolate, and characterize various nucleic acid sequences of biological interest. Nucleic acid hybridization has great potential in diagnosing disease states mediated by alteration in or additions to nucleic acid composition of the host. These alterations in nucleic acid composition will include genetic or environmental change in DNA by insertions, deletions, rearrangements, point mutations, or acquiring foreign DNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentration of disease related DNA or RNA present in a patient's body fluid and the unavailability of a sufficiently sensitive rapid method of DNA hybridization analysis.

Current methods for detecting DNA probes generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a carefully controlled temperature to remove unbound and nonspecifically bound probe without removing specifically bound probe. The support is then dried and the hybridized material is detected by autoradiography or by colorimetric methods. When very low concentrations must be detected, the ratio of specific to non-specifically bound probe can be very low and repeated washing under highly stringent conditions is frequently required. Under these conditions the sensitivity of the assay is often compromised because of substantial loss of specifically bound probe and failure to achieve a high enough specific to non-specific binding ratio to permit easy detection. When very low concentrations must be detected, the current methods are slow and labor intensive and non-isotopic labels that are less readily detected than radiolabels are frequently not suitable.

The use of $^{32}P$ nucleotide as a nucleic acid probe label is not desirable for several reasons. First, $^{32}P$ has a relatively short half life of 14.2 days. Consequently, the complementary probe DNA must be prepared just prior to the hybridization procedure to achieve maximum sensitivity. Secondly, the high decay energy of $^{32}P$ creates handling and disposal problems and undesirable hazards. It would therefore be advantageous in most cases to utilize a label which is less hazardous and prolongs the shelf life of the probe. High specific activity tritium labelled probes present one alternative. While tritium has not generally been found useful in previous hybridization methods which requires extended exposure times for detection by autoradiography, a solution method which detects labelled probe by liquid scintillation counting would be highly sensitive and desirable. Another less energetic isotope than $^{32}P$ but with a long half life is carbon-14.

The development of non-radioactive labeling of nucleic acid probes presents another alternative. A sensitive non-radioactive DNA labelling systems is described by Langer, et al., *Proc. Nat. Acad. Sci., USA,* 78, 6633 (1981). The system is based on the incorporation of a biotinylated deoxyuridine triphosphate into the DNA probe by the nick translation procedure. The resultant biotinylated DNA probe is stable and behaves as does a non-Diotinylated DNA probe. Detection of the biotinylated DNA has been applied to the detection of specific DNA and RNA sequences in fixed cells or in tissues following in situ hybridizations and also in hybridizations of DNA fragments separated by gel electrophoresis and transferred onto nitrocellulose filters. The detection of the hybridized biotinylated probe is accomplished by either fluorescent antibody or enzyme amplification techniques. These techniques are further described by Gardner, *BioTechniques,* 1, 38 (1983) and Lewin, *Science,* 221, 1167 (1983).

Other non-radioactive methods which have been described involve conjugating a fluorescent molecule such as tetramethylrhodamine or fluorescein isothiocyanate, to the 3'-terminus of single stranded RNA. These fluorescent RNA probes have been applied to cytochemical hybridizations. Bauman, et al., *J. Histochem. Cytochem,* 29, 227–238 (1981).

A method for increasing sensitivity to permit the use of a simple, rapid, (nonisotopic), homogeneous or heterogeneous method for detecting nucleic acid sequences is necessary.

2. Description of the Prior Art

Langer, et al., *Proc. Natl. Acad. Sci. USA,* (1981) 78, 6633–6637 discloses the enzymatic synthesis of biotin labelled polynucleotides and the use of these materials as novel nucleic acid affinity probes. The detection of viral genomes in cultured cells and paraffin imbedded tissue sections using biotin labelled hybridization probes is discussed by Brigati, et al., *Virology,* (1983) 126, 32–50. U.S. Pat. No. 4,486,539 discloses the detection of microbial nucleic acids by a one step sandwich hybridization test. Sensitive tests for malignancies based on DNA detection is described in U.S. Pat. Nos. 4,490,472. 4,480,040 discloses the sensitive and rapid diagnosis of plant viroid diseases and viruses employing radioactively labelled DNA that is complementary to the viroid or to the nucleic acid of the virus being diagnosed. European Patent Application EPO 302 175 A2, published Feb. 8, 1989, to Engelhardt, et al.

Priority U.S. patent application No. 391,440 filed Jun. 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153.

Detection and isolation of homologous, repeated and amplified nucleic acid sequences is disclosed in U.S. Pat. No. 4,675,283. A single stranded self-hybridizing nucleic acid probe capable of repeatedly hybridizing to itself or other nucleic acids to form an amplified entity is described in U.S. patent application Ser. No. 888,058, filed Jul. 22, 1986. U.S. Pat. Nos. 4,683,195 and 4,683,202 disclose a homogeneous polynucleotide displacement assay with digestion of the displaced RNA single strand polynucleotide from the reagent complex and amplifying nucleic acid sequences with treatment of separate complementary strands of the nucleic acid with two oligonucleotide primers. European Patent Application No. 0200362 describes a process for amplifying, detecting or cloning nucleic acid sequences and useful in disease diagnosis and in preparation of transformation vectors. A method for simple analysis of relative nucleic acid levels in multiple small samples by cytoplasmic dot hybridization is described in U.S. Pat. No. 4,677,054. A hybridization method of detecting nucleic acid sequences with a probe containing a thionucleotide is described in U.S. Pat. No. 4,647,529.

A simple and efficient enzymatic method for covalent attachment of DNA to cellulose and its application for hybridization-restriction analysis and for in vitro synthesis of DNA probes is described in *Nucleic Acids Research* (1986) 14:9171–9191. Cleavage of single stranded oligonucleotides by Eco RI restriction endonuclease is described in *Nucleic Acid Research* (1987) 15:709–716.

A nucleic acid hybridization assay employing probes cross-linkable to target sequences is described in U.S. Pat. No. 4,599,303. The method involves the preparation of a specific single stranded ribonucleic acid or deoxyribonucleic acid molecule into which a bifunctional cross-linking molecule has been covalently incorporated. The incorporation is such that the cross-linking molecule retains the capacity to undergo a second reaction with the nucleic acid of the bacterial, viral, or mammalian chromosome, which is the target for the probe such as to form a covalent cross link. Following cross-linking, the uncrossed link probe is separated from covalently cross-linked probe-target complex using one of several procedures which differentiate between single stranded probe and double stranded covalently linked probe-target complex.

Detection of target sequences in nucleic acids by hybridization using diagnostic and contiguous probes for diagnosis of genetic abnormality diseases, especially in an automated procedure, is described in European Patent Application No. 0 185 494A2. In the method a sample is hybridized with a probe complementary to a diagnostic portion of the target sequence (the diagnostic probe) and with a probe complementary to a nucleotide sequence contiguous with the diagnostic portion (the contiguous probe) under conditions wherein the diagnostic probe remains bound substantially only to the sample nucleic acid containing the target sequence. The diagnostic probe and contiguous probe are then covalently attached to yield a target probe that is complementary to the target sequence and the probes which are not attached are removed. In a preferred mode, one of the probes is labeled so that the presence or absence of the target sequence can then be tested by melting the sample nucleic acid target probe duplex, eluting the dissociated target probe, and testing for the label.

The above method suffers at least one disadvantage in that contiguous sequences are required. To carry out the method, one must identify the diagnostic sequence and the contiguous sequence and create diagnostic and contiguous probes complementary to the above sequences. If the diagnostic and contiguous sequences are not identified precisely, then the diagnostic and contiguous probes may not hybridize sufficiently and the assay specificity and sensitivity is lost or substantially decreased.

SUMMARY OF THE INVENTION

One aspect of the present invention involves a method for detecting the presence of a target nucleotide sequence which comprises (1) hybridizing a first nucleotide sequence and a second nucleotide sequence to non-contiguous portions of a target nucleotide sequence, (2) covalently attaching the first and second sequences when hybridized to the target sequence, and (3) determining the presence of covalently attached first and second sequences. The presence of the covalently attached first and second sequences is related to the presence of the target nucleotide sequence.

Another aspect of the present invention is a method for detecting a target nucleotide sequence wherein the following combination is provided in a liquid medium: (a) a sample suspected of containing a target nucleotide sequence, (b) a first nucleotide sequence complementary to a first portion of the target nucleotide sequence, (c) a second nucleotide sequence complementary to a portion of the target nucleotide sequence other than and non-contiguous with the first portion, and (d) means for covalently attaching the first and second sequences when the sequences are hybridized with the target nucleotide sequence. The combination is provided under conditions wherein the first and second sequences hybridize with the target nucleotide sequence and become covalently attached when the target nucleotide sequence is present. The presence of covalently attached first and second sequences is determined and the presence thereof indicates the presence of the target nucleotide sequence in the sample.

Another aspect of the present invention is a method for detecting a target nucleotide sequence which comprises providing the following combination in a liquid medium: (a) a sample suspected of containing a target nucleotide sequence, (b) a first nucleotide sequence complementary to a first portion of the target nucleotide sequence, (c) a second nucleotide sequence complementary to a portion of the target nucleotide sequence other than and non-contiguous with the first portion, (d) means for extending the second nucleotide sequence when the sequence is hybridized with the target nucleotide sequence to render the first and second nucleotide sequences contiguous, and (e) means for covalently attaching the first and second sequences. The combination is provided under conditions wherein the first and second sequences hybridize with the target nucleotide sequence if present, the second sequence is extended to render the sequence contiguous with the first sequence and the first and second sequences become covalently attached. The presence of covalently attached first and second sequences is determined and indicates the presence of the target nucleotide sequence in the sample.

Another aspect of the present invention is a method for detecting a target nucleotide sequence, which comprises combining in a liquid medium (a) a sample suspected of containing the target nucleotide sequence, (b) a first nucleotide sequence capable of binding to a first portion of the target sequence, and (c) a second nucleotide sequence capable of binding to a portion of the target sequence other than and non-contiguous with the first portion. The above are combined in the liquid medium under conditions wherein the first and second nucleotide sequence is hybridized with the target sequence. Means for covalently attaching the first and second nucleotide sequences when the sequences are hybridized to the target sequence are added to the medium. Then a determination is made whether the first and second sequences have become covalently attached. This determination provides an indication of the presence of the target sequence in the sample since the first and second sequences will become covalently attached only if the target sequence is present in the sample.

Another aspect of the present invention involves a method for detecting a target nucleotide sequence, which comprises providing in a liquid medium the following: (a) a sample suspected of containing a target nucleotide sequence, (b) a first nucleotide sequence that is capable of binding to a portion of the target nucleotide sequence and has, or is capable of having, means for immobilizing the first nucleotide, (c) a second nucleotide sequence that is non-contiguous with the first nucleotide sequence and is capable of binding to a portion of the target nucleotide sequence other than the portion to which the first nucleic acid sequence binds and that has, or is capable of having, a reporter group, and (d) means for causing the first nucleotide sequence to become covalently bound to the second nucleotide sequence. The medium is incubated under conditions wherein the first and second nucleotide sequences are (1) hybridized with the nucleotide sequence if present and (2) become covalently bound to one another. The first nucleotide sequence is separated from the medium. The separated first nucleotide sequence is examined for the presence of the second nucleotide sequence. The presence of the second nucleotide sequence with the first nucleotide sequence indicates the presence of the target nucleotide sequence in the sample.

In another aspect of the present invention a method for detecting the presence of a target nucleotide sequence is disclosed. The method comprises combining in a liquid medium (1) a sample suspected of containing a target nucleotide sequence, (2) a first nucleotide sequence complementary to a first portion of the target sequence and (3) a second nucleotide sequence complementary to a portion of the target sequence other than and non-contiguous with the first portion. At least one of the first and second nucleotide sequences has a small organic molecule bound to it and the other is bound or has the capacity for binding to a reporter group. The combination is made under conditions wherein the first and second nucleotide sequences bind to the target sequence. A polynucleotide polymerase and deoxynucleoside triphosphates are added to the medium under conditions wherein the second nucleotide sequence is extended to become contiguous with the first nucleotide sequence. Next, a ligase is added to the medium under conditions wherein the first and second nucleotide sequences become covalently attached. A surface is then added to the medium. The surface has a binding partner for the small organic molecule. Under the conditions of the assay the first nucleotide sequence becomes bound to the surface. The surface is separated from the medium and examined for the presence of the reporter group. The presence of the reporter group indicates the presence of the target nucleotide sequence in the sample.

The invention further includes compositions of matter and kits for detecting the presence of target nucleotide sequences.

DESCRIPTION OF THE SPECIFIC EMBODIMENTS

As mentioned above the present invention concerns methods for detecting the presence of a target nucleotide sequence. One embodiment of the invention involves hybridizing a first nucleotide sequence and a second nucleotide sequence to non-contiguous portions of a target nucleotide sequence covalently attaching the first and second sequences when the sequences are hybridized to the target sequence, and determining the presence of covalently attached first and second sequences. The presence of covalently attached first and second sequences indicates the presence of the target nucleotide sequence.

Before proceeding further with a description of the specific embodiments of the present invention, a number of terms will be defined.

Polynucleotide analyte—a compound or composition to be measured which is a polynucleotide having about 20 to 500,000 or more nucleotides, usually about 100 to 200,000 nucleotides, more frequently 500 to 15,000 nucleotides. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

| Microorganisms of interest include: | |
|---|---|
| Corynebacteria | |
| *Corynebacerium diptheria* | |
| Pneumococci | |
| *Diplococcus pneumoniae* | |
| Streptococci | |
| *Streptococcus pyrogenes* | |
| *Streptococcus salivarus* | |
| Staphylococci | |
| *Staphylococcus aureus* | |
| *Staphylococcus albus* | |
| Neisseriae | |
| *Neisseria meningitidis* | |
| *Neisseria gonorrhea* | |
| Enterobacteriaciae | |
| *Escherichia coli* | |
| *Aerobacter aerogenes* | The colliform bacteria |
| *Klebsiella pneumoniae* | |
| *Salmonella typhosa* | |
| *Salmonella choleraesuis* | The Salmonellae |
| *Salmonella typhimurium* | |
| *Shigellae dysenteria* | |
| *Shigellae schmitzii* | |
| *Shigellae arabinotarda* | The Shigellae |
| *Shigellae flexneri* | |
| *Shigellae boydii* | |
| *Shigellae sonnei* | |
| Other enteric bacilli | |
| *Proteus vulgaris* | |

TABLE I-continued

Microorganisms of interest include:

| | |
|---|---|
| Proteus mirabilis | Proteus species |
| Proteus morgani | |
| Pseudomonas aeruginosa | |
| Alcaligenes faecalis | |
| Vibrio cholerae | |
| Hemophilus-Bordetella group | Rhizopus oryzae |
| Hemophilus influenza, H. ducryi | Rhizopus arrhizua |
| Hemophilus hemophilus | Phycomycetes |
| Hemophilus aegypticus | Rhizopus nigricans |
| Hemophilus parainfluenzae | Sporotrichum schenkii |
| Bordetella pertussis | Flonsecaea pedrosoi |
| Pasteurellae | Fonsecaea compact |
| Pasteurella pestis | Fonsecacea dermatidis |
| Pasteurella tulareusis | Cladosporium carrioni |
| Brucellae | Phialophora verrucosa |
| Brucella melitensis | Aspergillus nidulans |
| Brucella abortus | Madurella mycetomi |
| Brucella suis | Madurella grisea |
| Aerobic Spore-forming Bacilli | Alleschería boydii |
| Bacillus anthracis | Phialophora jeanselmei |
| Bacillus subtilis | Microsporum gypsum |
| Bacillus megaterium | Trichophyton mentagrophytes |
| Bacillus cereus | Keratinomyces ajelloi |
| Anaerobic Spore-forming Bacilli | Microsporum canis |
| Clostridium botulinum | Trichophyton rubrum |
| Clostridium tetani | Microsporum adouini |
| Clostridium perfringens | Viruses |
| Clostridium novyi | Adenoveruses |
| Clostridium septicum | Herpes Viruses |
| Clostridium histolyticum | Herpes simplex |
| Clostridium tertium | Varicella (Chicken pox) |
| Clostridium bifermentans | Herpes Zoster (Shingles) |
| Clostridium sporogenes | Virus B |
| Mycobacteria | Cytomegalovirus |
| Mycobacterium tuberculosis | Pox Viruses |
| hominis | Variola (smallpox) |
| Mycobacterium bovis | Vaccinia |
| Mycobacterium avium | Poxvirus bovis |
| Mycobacterium leprae | Paravaccinia |
| Mycobacterium paratuberculosis | Molluscum contagiosum |
| Actinomycetes (fungus-like | Picornaviruses |
| bacteria) | Poliovirus |
| Actinomyces Isaeli | Coxsackievirus |
| Actinomyces bovis | Echoviruses |
| Actinomyces naeslundii | Rhinoviruses |
| Nocardia asteroides | Myxoviruses |
| Nocardia brasiliensis | Influenza (A, B and C) |
| The Spirochetes | Parainfluenza (1–4) |
| Treponema pallidum Spirillum | Mumps Virus |
| minus | Newcastle Disease Virus |
| Treponema pertenue | Measles Virus |
| Streptobacillus | Rinderpest Virus |
| monoiliformis | Canine Distemper Virus |
| Treponema carateum | Respiratory Syncytial Virus |
| Borrelia recurrents | Rubella Virus |
| Leptospira icterohemorrhagiae | Arboviruses |
| Leptospira canicola | Eastern Equine Eucephalitis |
| Trypanasomes | Virus |
| Mycoplasmas | Western Equine Eucephalitis |
| Mycoplasma pneumoniae | Virus |
| Other pathogens | Sindbis Virus |
| Listeria monocytogenes | Chikugunya Virus |
| Erysipelothrix rhusiopathiae | Semliki Forest Virus |
| Streptobacillus moniliformis | Mayora Virus |
| Donvania granulomatis | St. Louis Encephalitis Virus |
| Bartonella bacilliformis | California Encephalitis Virus |
| Rickettsiae (bacteria-like parasites) | Colorado Tick Fever Virus |
| | Yellow Fever Virus |
| Rickettsia prowazekii | Dengue Virus |
| Rickettsia mooseri | Reoviruses |
| Rickettsia rickettsii | Reovirus Types 1–3 |
| Rickettsia conori | Retroviruses |
| Rickettsia australis | Human Immunodeficiency |
| Rickettsia sibiricus | Viruses (HIV) |
| Rickettsia akari | Human T-cell Lymphotrophic |
| Rickettsia tsutsugamushi | Virus I & II (HTLV) |
| Rickettsia burnetti | Hepatitis |
| Rickettsia quintana | Hepatitis A Virus |
| Chlamydia (unclassifiable | Hepatitis B Virus |
| parasites bacterial/viral) | Hepatitis nonA-nonB Virus |
| Chlamydia agents (naming | Tumor Viruses |
| uncertain) | Rauscher Leukemia Virus |
| Fungi | Gross Virus |
| Cryptococcus neoformans | Maloney Leukemia Virus |
| Blastomyces dermatidis | Human Papilloma Viruses |
| Hisoplasma capsulatum | |
| Coccidioides immitis | |
| Paracoccidioides brasiliensis | |
| Candida albicans | |
| Aspergillus fumigatus | |
| Mucor corymbifer (Absidia corymbifera) | |

The polynucleotide analyte, where appropriate or necessary, will be treated to cleave the analyte to obtain a fragment that contains a target nucleotide sequence. Accordingly, the analyte can be cleaved by known techniques such as treatment with a restriction endonuclease or other site specific chemical or enzymatic cleavage method.

For purposes of this invention, the polynucleotide analyte or the cleaved fragment obtained from the polynucleotide analyte will usually be at least partially denatured or single stranded or treated to render it denatured or single stranded. Such treatments are well known in the art and include, for instance, heat or alkali treatment. For example, double stranded DNA can be heated at 90°–100° C. for a period of about 1 to 10 minutes under suitable conditions of ionic strenghth to produce denatured material.

Target nucleotide sequence—at least a portion of a sequence of nucleotides to be identified, the identity of which is known to an extent sufficient to allow preparation of non-contiguous binding polynucleotide sequences that will hybridize with non-contiguous portions of such target sequence. The target nucleotide sequence usually will contain from about 12 to 1000 or more nucleotides, preferably 15 to 100 nucleotides. The target nucleotide sequence will generally be a fraction of a larger molecule or it may be substantially the entire molecule. The minimum number of nucleotides in the target polynucleotide sequence will be selected to assure that the presence of nucleotide analyte can be determined. The maximum number of nucleotides in the target sequence will normally be governed by the length of the polynucleotide analyte and its tendency to be broken by shearing, by endogenous nucleases or by reagents used to cleave the target sequence.

First nucleotide sequence-a compound capable of hybridizing with the target nucleotide sequence by virtue of having a polynucleotide sequence complementary to a region of the target nucleotide sequence such that the first nucleotide sequence will become bound to such region of the target nucleotide.

The first nucleotide sequence can be obtained by biological synthesis or by chemical synthesis. For short sequences (up to 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target nucleotide sequence. The first nucleotide sequence can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as those employed in commercial kits for preparation of RNA (e.g. from Promega) and by the use of M13 for single stranded DNA as described by J. Messing (1983) *Methods Enzymol*, 101, 20–78.

Other methods of oligonucleotide synthesis include phosphotriester and phosphodiester methods (Narang, et al. (1979) *Meth. Enzynol* 68:90) and synthesis on a support (Beaucage, et al. (1981) *Tetrahedron Letters* 22:1859–1862) as well as phosphoramidate technique, Caruthers, H. H., et al., "Methods in Enrymology," Vol. 154, pp. 287–314 (1988), and others described in "Synthesis and Applications of DNA and RNA," S. A. Narang editor, Academic Press, New York, 1987, and the references contained therein.

The major criteria for choosing the first nucleotide sequence are: (1) The sequence should be reliable, that is, the region to be synthesized must be known accurately and should be specific for the polynucleotide analyte. (2) The sequence should be of sufficient length to provide stable and specific binding. The minimum sequence will usually be at least 4 nucleotides in length. In general, synthetic polynucleotides will be about 8 to 300 nucleotides, more frequently 15 to 50 nucleotides in length. The combined length of the hybridizing portion of the first and second nucleotide sequences is at least about 20 nucleotides, preferably about 30 to 3000 nucleotides, in length. With biologically synthesized polynucleotides random fragments of unknown sequences may be used provided, however, that nucleic acids are single stranded and complementary to the polynucleotide analyte.

Second nucleotide sequence—The second nucleotide sequence is capable of hybridizing with the target nucleotide sequence at a region other than and non-contiguous with that with which the first nucleotide sequence hybridizes. The second nucleotide sequence may be ascertained and prepared as described above for the first nucleotide sequence.

The two non-contiguous regions of the target nucleotide sequences complementary to the first and second nucleotide sequences will normally be in reasonable proximity to, but not contiguous with, one another to ensure that a substantial fraction of the analyte will have the two regions linked. The two regions may be within 1 to 3 nucleotides without the need for chain extension where the enzyme used for ligation can ligate the sequences when non-contiguous. Where chain extension of the second nucleotide sequence is employed, the two regions will usually be within 5,000 bases, frequently within 2,000 bases, more frequently within 500 bases, but may be separated by 10,000 bases or higher, particularly when the assay is used to demonstrate linkage of two nucleic acid sequences.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs, such as biotin-avidin, hormones-hormone receptors, nucleic acid duplexes, IgG-protein A, DNA-DNA, DNA-RNA, and the like, are not immunological pairs but are included within the scope of this invention.

Ligand any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Small organic molecule—a compound of molecular weight less than 1500, preferably 700 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, 3. *Biol. Chem.*, 245:3059 (1970). The surface can have any one of a number of shapes, such as strip, rod, particle, including bead, and the like.

The surface will usually be polyfunctional or be capable of being polyfunctionalized or be capable of binding an oligonucleotide or an sbp member through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.* 245,3059 (1970). The length of a linking group to the oligonucleotide or sbp member may vary widely, depending upon the nature of the compound being linked, the effect of the distance between the compound being linked and the particle on the hybridization of the sequences and the like. The oligonucleotide or sbp member will be substantially bound to the outer surface of the particle.

Particles employed as the surface can be fluorescent either directly or by virtue of fluorescent compounds or fluorescers bound to the particle in conventional ways. The fluorescers will usually be dissolved in or bound covalently or non-covalently to the particle and will frequently be substantially uniformly bound through the particle. Fluoresceinated latex particles are taught in U.S. Pat. No. 3,853,987 and are available commercially as Covaspheres from Covalent Technology Corp.

Label or reporter group-A member of the signal producing system that is conjugated to or becomes bound to the first or second nucleotide sequences or to one or more nucleotides that are employed to render the first and second nucleotide sequences contiguous when these are hybridized to the target sequence. Preferably, one of the first or second sequences and one or more of the nucleotides will have, or be capable of having, a label. In general, any label that is detectable can be used. The label can be isotopic or nonisotopic, usually non-isotopic, and can be a catalyst, dye, fluorescent molecule, chemiluminescer, coenzyme, enzyme, substrate, radioactive group, a particle such as latex or carbon particle, metalsol, crystallite, liposome, cell, etc., which may or may not be further labeled with a dye, catalyst or other detectible group, and the like. The label is a member of a signal producing system and can generate a detectable signal either alone or together with other members of the signal producing system. The label can be bound directly to the first or second nucleotide sequence or intervening nucleotide sequence or can become bound thereto by being bound to an sbp member complementary to an sbp member that is bound to the first or second nucleotide sequence or the intervening nucleotide sequence.

Signal Producing System—The signal producing system may have one or more components, at least one component being the label or reporter group. The signal producing system generates a signal that relates to the presence or amount of polynucleotide analyte in a sample. The signal producing system includes all of the reagents required to produce a measurable signal. When the label is not conjugated to the first or second nucleotide sequence or the intervening nucleotide sequence, the label is normally bound to an sbp member complementary an sbp member that is part of the first or second nucleotide sequence. Other components of the signal producing system may be included in a developer solution and can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of polynucleotide analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and β-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

The signal producing system can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/ml, and composed of material that can be transparent, partially transparent, or opaque.

The organic particles will normally be comprised of polymers, either addition or condensation polymers, which are readily dispersible in the assay medium. The surface of particles will be adsorptive or functionalizable so as to bind, either directly or indirectly, the oligonucleotide or an sbp member. The nature of particles is described above.

Fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminostilbenes immines, anthracenes, oxacarboxyanine, merocyanine, 3-aminoequilenin, perylene, bis-benzoxazole, bis-p-oxazolyl benzene, 1,2-benzophenazine, retinal, bis-3 -aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference.

Additionally, energy absorbent or quenching particles can be employed which are solid insoluble particles of at least about 50 nm in diameter capable of quenching the fluorescence of the fluorescent particle when within the distance resulting from hybridization of a probe with the polynucleotide analyte or from specific binding between members of specific binding pairs. The quenching particle may be the same or different, usually different, from the fluorescent particle. Normally, the quenching particle will provide a substantial quenching at a distance of more than about 50 Å, preferably more than about 500 Å, more preferably more than about 2000 Å, where the distance is measured from the surfaces of the particles.

Many different types of particles may be employed for modulating light emission. Of particular interest are carbon particles, such as charcoal, lamp black, graphite, colloidal carbon and the like. Besides carbon particles metal sols may also find use, particularly of the noble metals, gold, silver, and platinum. Other metal-derived particles may include metal sulfides, such as lead, silver or copper sulfides or metal oxides, such as iron or copper oxide.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino analog of the above compound. Other members of the family include the 5-amino-6,7,8-trimethoxy- and the dimethylamine-[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino- and para-methoxy-substituents. chemiluminescence may also be obtained with oxilates, usually oxalyl, active esters, e.g., p-nitrophenyl and a peroxide, e.g., hydrogen peroxide, under basic conditions. Alternatively, luciferins may be used in conjunction with luciferase or lucigenins.

Ancillary Materials—various ancillary materials will frequently be employed in the assay in accordance with the present invention. For example, buffers will normally be present in the assay medium, as well as stabilizers for the assay medium and the assay components, Frequently, in addition to these additives, proteins may be included, such as albumins, or surfactants, particularly non-ionic surfactants, binding enhancers, e.g., polyalkylene glycols, or the like.

Nucleoside triphosphates—a nucleoside having a 5' triphosphate substituent, usually a deoxynucleoside triphosphate. The nucleosides are pentose sugar derivatives of nitrogenous bases of either purine or pyrimidine derivation, covalently bonded to the 1'-carbon of the penrose sugar. The purine bases include adenine(A), guanine(G), and derivatives and analogs thereof. The pyrimidine bases include cytosine (C), thymine (T), uracil (U), and derivatives and analogs thereof.

The derivatives and analogs are exemplified by those that are recognized and polymerized in a similar manner to the underiviatized nucleotide triphosphates. Examples of such derivatives or analogs by way of illustration and not limitation are those which are modified with a reporter group, biotinylated, amine modified, radiolabeled, alkylated, and the like and also include thiophosphate, phosphite, ring atom modified derivatives, and the like. The reporter group can be a fluorescent group such as fluoroscein, a chemiluminescent group such as luminol, a terbium chelator such as N-(hydroxyethyl) ethylenediaminetriacetic acid that is capable of detection by delayed fluorescence, and the like.

Polynucleotide polymerase—a catalyst, usually an enzyme, for forming an extension of the second nucleotide sequence along the target nucleotide where the extension is complementary thereto. The polynucleotide polymerase utilizes the nucleoside triphosphates as the building blocks for the extension which proceeds in a 5' to 3' (3' to 5' with respect to the target) direction until the second. nucleotide sequence is contiguous with the first nucleotide sequence. Usually, the catalysts are enzymes, such as RNA polymerases, preferably DNA polymerases such as, for example, prokaryotic DNA polymerase (I, or III), T4 DNA polymerase, T7 DNA polymerase, Klenow fragment, reverse transcriptase, RNA replicases, and the like derived from any source such as cells, bacteria, such as *E. coli*, plants, animals, virus, thermophilic bacteria, and so forth.

Wholly or partially sequentially—when the sample and various agents utilized in the present invention are combined other than simultaneously, one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of the nucleotide sequences to hybridize is based on the complementarity of the nucleotide sequence, which in turn is based on the pairing of complementary nucleotides. The more a given sequence contains nucleotides complementary to another sequence, the greater the degree of hybridization of the first to the second.

Non-contiguous—the first nucleotide sequence and the second nucleotide sequence are hybridized to non-contiguous portions of the target nucleotide sequence, there being at least one nucleotide present in the target sequence between the hybridized 5' terminus of the first nucleotide sequence and the 3' end of the second nucleotide sequence.

Contiguous—the first nucleotide sequence and the second nucleotide sequence are considered to be contiguous when there are no nucleotides between the 5' end of the first nucleotide sequence and the 3' end of the second nucleotide sequence, when these nucleotide sequences are hybridized with the target nucleotide sequence.

Covalently attaching—forming a chemical bond between the first nucleotide sequence and the second nucleotide sequence. The chemical bond can be formed whether the first and second nucleotide sequences are contiguous or not when the sequences are bound to the target nucleotide sequence. Covalent attachment can be achieved enzymatically, for example by utilizing a ligase. Prior to ligating the first and second nucleotide sequences, the second nucleotide sequence, or the sequence having a 3' terminus extendable in the direction of the other hybridized nucleotide sequence, generally must be treated to render it contiguous or effectively contiguous with the first nucleotide sequence. The sequences are effectively contiguous, for example, when enzymatic ligation or a chemical coupling can take place. Generally, the first and second nucleotide sequences are effectively contiguous when they are within 1 to 3 nucleotides apart. Chain extension may be achieved, for example, by adding a polynucleotide polymerase and nucleoside triphosphates or by ligating to the first and second nucleotide sequences a nucleotide sequence complementary to the non-contiguous region of the target nucleotide sequence between the first and second nucleotide sequences. The covalent attachment may be achieved chemically by forming chemical bonds between the phosphate moeities of the first and second nucleotide sequences. Alternatively, the first and second nucleotide sequences may be linked together as part of a helix so that rendering the first and second nucleotide sequences contiguous is not necessary. In another embodiment the covalent attachment may be achieved by photochemistry wherein the first and second nucleotide sequences are photocoupled.

Means for extending the second nucleotide sequence—in order to ligate the first and second nucleotide sequences when the sequences are bound with the target nucleotide sequence it is necessary to render the first and second nucleotide sequences contiguous. As explained above, the second nucleotide sequence can be extended by combining the second nucleotide sequence hybridized to the target nucleotide sequence with a polynucleotide polymerase and nucleoside triphosphate under conditions for extending the second nucleotide sequence. Alternatively, a nucleotide sequence complementary to the non-contiguous portion of the target nucleotide sequence between the first and second nucleotide sequences can be ligated to the second nucleotide sequence.

One embodiment of the present invention concerns a method for detecting the presence of a target nucleotide sequence. The method comprises hybridizing the first nucleotide sequence and the second nucleotide sequence to non-contiguous portions of a target nucleotide sequence. The first and second sequences are covalently attached when hybridized to the target sequence. The presence of covalently attached first and second sequences indicates the presence of the target nucleotide sequence.

Generally, a combination is provided in a liquid medium comprising a sample suspected of containing a target nucleotide sequence, a first nucleotide sequence complementary to a first portion of the target nucleotide sequence, a second nucleotide sequence complementary to a portion of the target nucleotide sequence other than and not contiguous with the first portion and means for covalently attaching the first and second sequences when these sequences are hybridized with the target nucleotide sequence. The combination is provided under conditions wherein the first and second sequences are hybridized with the target nucleotide sequence and become covalently attached when the target nucleotide sequence is present.

The order of combining of the various reagents to form the combination may vary and can be simultaneous or wholly or partially sequential. Generally, a sample containing a target nucleotide sequence is obtained. This may be combined with a pre-prepared combination of first and second nucleotide sequences, nucleoside triphosphates, and polynucleotide polymerase, followed by addition of a ligase. However, simultaneous addition of the above, as well as other step-wise or sequential orders of addition, may be employed. The concentration and order of addition of reagents and conditions for the method are governed generally by the desire to optimize hybridization of all the first and second nucleotide sequences with the target nucleotide sequence and covalent attachment of the so-hybridized first and second nucleotide sequences.

One means for covalently attaching the first and second sequences when these sequences are hybridized with the target nucleotide sequence involves the chain extension of the second nucleotide sequence to render the first and second nucleotide sequences contiguous. One means for extending the second nucleotide sequence comprises adding a polynucleotide polymerase and deoxynucleoside triphosphates to the liquid medium and incubating the medium under conditions for forming a chain extension at the 3' end of the second nucleotide sequence to render it contiguous with the first nucleotide sequence when these sequences are hybridized with the target sequence.

When the first and second nucleotide sequences are rendered contiguous when hybridized with the target sequence, the first and second nucleotide sequences are then covalently attached. One method of achieving covalent attachment of the first and second nucleotide sequences is to employ enzymatic means. Preferably the medium containing the first and second nucleotide sequences hybridized with the target sequence can be treated with a ligase, which catalyzes the formation of a phosphodiester bond between the 5' end of one sequence and the 3' end of the other.

Any enzyme capable of catalyzing the reaction of the polynucleotide 3'-hydroxyl group can be employed. Examples, by way of illustration and not limitation, of such enzymes are polynucleotide ligases from any source such as *E. coli* bacterial ligase, T4 phage DNA ligase, mammalian DNA ligase, and the like. The reaction components referred to above additionally can include an oligonucleotide terminated at the 3' end with a group that does not react to provide chain extension by the polynucleotide polymerase. Terminal transferases such as terminal deoxynucleotidyl transferases can be employed together with a dideoxynucleoside triphosphate, methylated nucleoside triphosphate, or the like. Such reagents and reactions are well known in the art for other applications and further detailed discussion is not necessary here. The pH, temperature, solvent, and time considerations will be similar to those described above for the method of the invention.

In another embodiment the two polynucleotide sequences can be covalently attached by employing chemical means. One such chemical means involves the formation of a phosphoimidate on one of the sequences. A hydroxyl group on the sugar moiety of the contiguous nucleotide will react with the phosphoimidate to form a chemical bond resulting in a phosphate. Other phosphoimidates on phosphate groups of non-contiguous nucleotides will be hydrolized under the reaction conditions.

Another method for forming a chemical bond involves the formation in one of the first or second nucleotide sequences of a carbamate on the sugar moiety wherein the carbamate involves, for example, a pyridol moiety. The hydroxyl group of the sugar moiety of the contiguous nucleotide will then displace the pyridol group to result in covalent bond formation.

In another approach the hydroxyl group on the sugar moiety of a nucleotide of the first or second sequences can be derivatized to form a disulfide, which can be used to ligate the two sequences. See Chu, et al. (1988) *Nucleic Acids Research,* 16(9): 3671–3691.

In another approach the hydroxyl group of the sugar moiety of the contiguous nucleotide can be tosylated and the subsequent reaction will result in a covalent bond formation between the first and second nucleotide sequences. Such an approach is generally described in Imazawa, M., et al., *Chem. Pharm. Bull.,* 23 (3), 604–610 (1975) and Nagyvary, J., et al., *J. Org. Chem.,* 45 (24), 4830–4834 (1980), In another approach the hydroxyl group of the sugar moiety of one of the contiguous nucleotides can be activated with carbodiimide and the sugar moiety of a contiguous nucleotide can contain an amine group. The amine group will react with the activated carbodiimide of the contiguous nucleotide to result in covalent bond formation. Such a reaction is described in Dolinnaya, N. G., et al., *Bioorg. Khim.,* 12 (6), 755–763 (1986) and Dolinnaya, N. G., et al., *Bioorg. Khim.,* 12 (7), 921–928 (1986)

In another approach a protected sulfhydryl group can be formed on one of the sugar moieties of the contiguous nucleotide, This sulfhydryl group can be then reacted with a maleimide on the contiguous nucleotide to result in covalent bond formation.

In another approach for chemically forming the covalent attachment between the first and second nucleotide sequences, a photoreaction can be employed. For example, one of the contiguous nucleotides can be treated to form an aryl azide and then the material can be irradiated to result in a covalent bond formation between the contiguous nucleotides.

Another means for achieving the covalent attachment of the first and second nucleotide sequences when the sequences are hybridized to non-contiguous portions of the target nucleotide sequence involves the use of a nucleotide sequence that is sufficiently complementary to the non-contiguous portion of the target nucleotide sequence lying between the first and second nucleotide sequences. For purposes of this description such a nucleotide sequence will be referred to as an intervening linker sequence. The linker sequence can be prepared by known methods such as those described above for the preparation of the first and second nucleotide sequences. The linker sequence can be hybridized to the target sequence between the first and second nucleotide sequences. The linker sequence can then be covalently attached to both the first and second nucleotide sequence utilizing enzymatic or chemical means as referred to above. It is also possible to utilize combinations of linker sequences and polymerase to achieve a contiguous relationship between the first and second nucleotide sequences when these sequences are bound to the target nucleotide sequence.

Another means for covalently attaching the first and second nucleotide sequences when the sequences are hybridized to the target nucleotide sequence in a non-contiguous relationship involves chain extension of the second nucleotide sequence followed by carbodiimide coupling of the two sequences as described by Dolinnaya, et al. (1988), *Nucleic Acids Research,* 16 (9): 3721–3938.

In carrying out the method of the invention an aqueous medium will be employed. Other polar cosolvents may also be employed, usually oxygenated organic solvents of from 1–6, more usually from 1–4, carbon atoms, including alcohols, ethers and the like. Usually these cosolvents will be present in less than about 70 weight percent, more usually in less than about 30 weight percent.

The pH for the medium will usually be in the range of about 4.5 to 9.5, more usually in the range of 5.5–8.5, and preferably in the range of about 6–8. The pH and temperature are chosen and varied, as the case may be, so as to provide for either simultaneous or sequential hybridization of the target sequence with the first and second nucleotide sequences extension of the second nucleotide sequence, and covalent attachment of the first and second nucleotide sequences. In some instances, a compromise will be made between these considerations depending on whether the above steps are performed sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method and desirably constant temperatures during the period for conducting the method. The temperatures for the method will generally range from about 20° to 90° C., more usually from about 30° to 70° C. preferably 37° to 50° C. However, the temperature can be varied depending on whether the above steps are carried out sequentially or simultaneously. For example, relatively low temperatures of from about 20° to 40° C. can be employed for the chain extension step, while denaturation and hybridization can be carried out at a temperature of from about 40° to 80° C.

The time period for carrying out the method of the invention will generally be long enough to achieve covalent attachment between the first and second nucleotide sequences, when these sequences are attached to the target nucleotide sequence and determining whether such covalent attachment has occurred. Generally, the time period for conducting the method will be from about 5 to 200 min. As a matter of convenience, it will usually be desirable to minimize the time period.

The concentration of the target nucleotide sequence to be determined can be as low as $10^{-21}$M in a sample but will generally vary from about $10^{-14}$M to $10^{-19}$M, more usually from about $10^{-16}$ to $10^{-19}$M. The concentration of the first and second nucleotide sequence and the deoxynucleoside triphosphates in the medium can vary widely. Preferably, these reagents will be present in large molar excess over the amount of target nucleotide sequence expected. The deoxynucleoside triphosphates will usually be present in $10^{-6}$ to $10^{-2}$M, preferably $10^{-5}$ to $10^{-3}$M. The second nucleotide sequences, as well as the first nucleotide sequence, will usually be present in at least$10^{-12}$M, preferably $10^{-10}$M, more preferably at least about $10^{-8}$M.

The concentration of the polymerase and any cofactors in the medium can also vary substantially. These reagents may be present in as low as $10^{-12}$M but may be present in a concentration at least as high or higher than the concentration of the first and second nucleotide sequences, the primary limiting factor being the cost of the reagents, which are usually enzymes. The final concentration of each of the reagents will normally be determined empirically to optimize the present method with respect to both speed and sensitivity.

It can be desirable, and indeed preferable in some circumstances, that the first or second nucleotide sequence has, or is capable of having, means for immobilizing the sequence. Generally, this means for immobilizing involves a support. Either the first or the second nucleotide sequence can be treated to bind the sequence to a support prior to the use of this sequence in the method of the present invention. Numerous methods are known for binding nucleotide sequences to solid supports. For example see T. Goldkorn et al., *Nucleic Acids Research* (1986) 14:9171–9191 and the references contained therein. Generally, the procedures for attaching the nucleotide sequence to supports involve chemical modifications of some of the nucleotides in the sequence whereby the sequence can then be attached to the support. Preferably, the bond between the support and the nucleotide sequence will be covalent, more preferably involving a linking group between the nucleotide sequence the support. For example, the support can be treated to introduce maleimide groups and one of the first or second nucleotide sequences can be treated to introduce a thiol group. The thiol group is reactive with the activated olefin of the maleimide group and in such a fashion the nucleotide sequence can be covalently bound to the support. Examples of other such linking groups are cellulose derivatized with diazobenzyloxymethyl groups as described by Noyes, B. E. and Start, G. R., *Cell* 5, 301 (1975) and Alwine, J. C., et al., *Proc. Natl. Acad. Sci.*, U.S.A. 74, 5350 (1977), and cellulose derivatized with o-aminophenylthioether, such as described by Seed, B., *Nucleic Acids Res.*, 10, 1799 (1982).

If the first or second nucleotide sequence is not initially bound to a support, it may be desirable that one of the two sequences become bound to a support at some time during the method of the invention, preferably, prior to the determination of whether the first or second sequences have become covalently attached when hybridized to the target sequence. Accordingly, the support and one of the nucleotide sequences must contain reactive groups which can provide a linkage between the support and the nucleotide sequence. The nature of the reactive groups will be such as to be compatible with the method of the present invention.

One such system is that described above where the support would contain maleimide groups and the nucleotide sequence would contain a thiol group. In another embodiment the nucleotide sequence and the support can contain complementary specific binding pair members such as biotin-avidin and the like. Thus, the method of the present invention can be run in solution and at the appropriate time the support can be introduced whereupon the complementary sbp members will bind. After the support is washed, a determination can then be made as to whether or not the first and second sequences have become covalently attached to one another.

Other examples of such systems are repressor-operator interactions where one of the nucleotide sequences is captured at the solid surface by its sequence specific interaction with a specific repressor or modulator protein immobilized on the solid surface. An advantage of this embodiment of the capture phase is that in some cases release of the operator DNA from the repressor can be accomplished by treating the complex with an inducer molecule. For example, the tetracycline repressor may be immobilized on a solid surface so that an operator sequence present on one or the other of the nucleotide sequences is specifically captured and retained when the solution is contacted to the surface. The surface may then be washed to eliminate any non-specific binding and finally the operator containing nucleotide may be released from the surface by contacting the repressor-operator complex board at the surface with an inducer molecule (tetracycline or one of its active analogs in this case).

The inducer molecule may be the "natural inducer" in the sense that it is structurally identical with the molecule in nature that causes dissociation of the biological/regulatory repressor-operator complex or it may be a synthetic analog of the natural inducer with similar or enhanced binding and complex dissociation activity. Examples of the above include the tetracycline repressor-operator interaction and its dissociation by tetracycline such as described by Hillen, W., et al., *J. Mol. Biol.*, 169, 707–721 (1983) and Klock, G., et al., *J. Bact.*, 161, 326–332 (1985).

In the situation where one of the first or second sequences is covalently attached to the support, it may be desirable to remove the attached sequence from the support, such as, for example, in order to amplify or clone the sequence. In this situation it is desirable to introduce a clearable group between the nucleotide sequence and the support. Exemplary of such cleavable groups are prophosphate linkages, disulfide linkages and restriction enzyme cleavage sites.

After provision has been made for covalently attaching the first and second nucleotide sequences when these sequences are hybridized with the target nucleotide sequence, if present, the presence of covalently attached first and second sequences is determined. The presence of covalent attachment indicates the presence of the target nucleotide sequence in the sample. Generally, this determination involves removing substantially all of the unbound nucleotide sequence that carries a label or a reporter group and examining the remainder for the presence of covalently attached first and second nucleotide sequences bearing a label. If one of the nucleotide sequences is bound, or becomes bound, to a support, the support is removed from the medium, washed free of unbound material, and then examined for the presence of a label or a reporter group. Generally, this examination involves contacting the support with the remaining members of a signal producing system in order to produce a signal in relation to the presence of the target nucleotide sequence in the sample.

Use of the method in accordance with the present invention allows a support to be washed under conditions that would normally be more vigorous than those used when hybridization is carried out without covalent attachment. Frequently the washing conditions will completely disassociate duplexes bound to the support. These conditions include solutions containing kaotropic agents such as urea either alone or in combination with other denaturants such as formamide used either at ambient or elevated temperature. The covalent attachment between the first and second nucleotide sequences and the bonding of one of the nucleotide sequences to a surface, however, will be unaffected. Detection of the resulting labelled material bound to the support will indicate the presence of the target nucleotide sequence in the sample.

Where the first nucleotide sequence is not bound to a surface or where a labeled nucleotide is being incorporated, an important feature in the covalent extension of the second nucleotide sequence is that the first nucleotide sequence is terminated at the 3' end with a group incapable of reacting in a chain extension reaction sequence by a polynucleotide polymerase. In this way chain extension along the first nucleotide sequence is prevented. Exemplary of such a group, by way of illustration and not limitation, are dideoxynucleotides, such as dideoxythymidine, dideoxyadenosine, dideoxyguanosine, and dideoxycytidine, isopropylphosphoryl, phosphate, N-(trimethyl ammonium ethyl) carbamoyl, polysaccharides such as dextran, polystyrene, hydrazones, proteins, and deoxyribose-3'-phosphoryl and the like.

Dideoxynucleotide capping can be carried out according to conventional techniques such as, described by Atkinson, et al. (1969) *Biochem.*, 8, 4897–4904. Hydrazone formation can be obtained by oxidation of a ribonucleotide at the 3' end with periodate to form a dialdehyde, which can then react with substituted hydrazines such as dinitrophenylhydrazine, positively charged hydrazines such as 2-trimethylammonium-1-ethylhydrazine, hydrazines bonded to dextran and proteins, particularly hydrazide derivatives of carboxyalkyldetrans and proteins, etc., and the like. Such 3' blocked material may then be separated from other reaction mixture components by affinity chomotography and other techniques well known in the art. Aldehyde formation followed by derivatization of the aldehyde is one general procedure for blocking the 3' end of the template. See, for example, Reines, et al. (1974) *Nucleic Acids Res.*, 1, 767–786. A 3'-terminal phosphate group can be achieved, for example, by treating the single stranded polynucleotide terminated with a ribonucleotide with periodate and β-elimination by cyclohexylamine or benzylamine (See Krynetskaya et al. (1986) *Nucleosides and Nucleotides*, 5(1): 33–43 or by T4 RNA ligase addition of pCp (3', 5'-diphosphate cytidine) such as is typically carried out in the 3' end labelling of DNA.

Terminal 3' blocking may also be achieved by covalent attachment of the 3' end to a glass bead, resin, or any other suitably modified particle or bead. This means of blocking the 3' functionality is commonly practiced under a number of forms in the synthesis of oligonucleotides. This approach can provide for attachment to a surface.

Detection of the signal will depend upon the nature of the signal producing system utilized. If the label or reporter group is an enzyme, additional members of the signal producing system would include enzyme substrates and so forth the product of the enzyme reaction is preferably a dye that can be detected spectrophotometrically. If the label is a fluorescent molecule the medium can be irradiated and the fluorescence determined. Where the label is a radioactive group, the medium can be counted to determine the radioactive count.

In another approach for detection of a signal, the second nucleotide sequence can be labelled with a "label sequence" that is present at the 5'-end of the second nucleotide sequence. This label sequence is hybridized with a third nucleotide sequence and a fourth nucleotide sequence. The third nucleotide sequence has two subsequences, one being a sequence complementary to the label sequence of the second nucleotide sequence and the other being a different sequence. The fourth nucleotide sequence will have a sequence complementary to the different sequence of the third nucleotide sequence and a sequence that is essentially identical to the label sequence of the second nucleotide sequence. One pair of complementary portions of the third and fourth nucleotide sequences is at the same end of the each probe (that is, 3' or 5') and the second pair, comprising the special sequence and its complementary sequence is at the other end of each probe. Hybridization of the labelled nucleotide sequence and the third and fourth nucleotide sequences will then form an extended chain, which extends from the labelled nucleotide sequence. Preferably the 3' ends of the third nucleotide sequence will be contiguous with the 5' ends of the adjoining third nucleotide sequence and the 3' ends of the fourth nucleotide sequence will be contiguous with the 5' ends of the adjoining fourth nucleotide sequence. After hybridization, the ends can be ligated with a ligase. Noncovalently bound third and fourth nucleotide sequences can be washed away. The ligated third and fourth nucleotide sequences may then be detected preferably by detection of a label bound to one or both. The third or fourth nucleotide sequences can be labelled as described earlier for the first and second nucleotide sequences.

In an alternate embodiment of the detection aspect of the present invention, an amplified signal produced by the formation of a labelled sequence in the above method can also be utilized in determining the presence of covalently attached first and second nucleotide sequences. The second nucleotide sequence can contain a label bound to the 5' end. The label may be comprised of a nucleotide sequence beginning and ending with a restriction site. Preferably, this nucleotide sequence will be the repeating sequence in an oligomer. The label provides a signal after it has been ligated to the first nucleotide sequence in accordance with the above method. For this purpose the ligated second nucleotide sequence is exposed to an additional polynucleotide sequence complementary to a portion of the second polynucleotide to yield a clearable duplex polynucleotide template, a polynucleotide polymerase, nucleoside triphosphates, and restriction enzymes suitable for cleaving the restriction sites. The resulting newly formed complementary nucleotide sequence will usually be about six to thirty nucleotides in length. This sequence can be detected directly or it can be amplified by use of additional quantities of the template complementary to at least a portion of the second nucleotide sequence that is blocked at its 3' end in accordance with the nucleic acid amplification method described in U.S. Pat. No. 4,994,368, filed Jul. 23, 1987, the disclosure of which is incorporated herein by reference in its entirety. Alternatively, a specific binding sequence complementary to the newly formed sequence and bound to the 3' end of a repeating template sequence as described in the above mentioned patent application can be employed.

As a matter of convenience, the reagents employed in the present invention can be provided in a kit in packaged combination with predetermined amounts of reagents for use in the present method in assaying for a polynucleotide analyte in a sample. For example, a kit useful in the present method can comprise in packaged combination with other reagents first and second nucleotide sequences, which can be labeled or bound to a support or can be provided with groups to render the sequence labeled or bound to a support. The kit can further include in the packaged combination nucleoside triphosphates such as deoxynucleoside triphosphates, e.g., deoxyadenosine triphosphate (dATP), deoxyguanosine triphosphate (dGTP), deoxycytidine triphosphate (dCTP) and deoxythymidine triphosphate (dTTP). The kit can further include a polynucleotide polymerase and also means for covalently attaching the first and second sequences, such as a ligase.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where reactivity and shelf life will permit.

EXAMPLES

The invention is demonstrated further by the following illustrative examples.

Materials and Methods

Nucleic Acids

A 124 base "reporter" DNA (124mer) was synthesized by the phosphoramidite method of Caruthers, M. H., et al., "Methods in Enzymology", vol. 154, pp. 287–314 (1988) on a Biosearch 8750 automated DNA synthesizer and contained the following sequence:

```
5' CGGCCAGTGAATTC
   TTTTTTTTTCTTCTT
   TTTTTTTTTCTTCTT
   TTTTTTTTTCTTCTT
   TTTTTTTTTCTTCTT
   TTTTTTTTTCTTCTT
   TTTTTTTTTCTTCTT
TTTTTTTTTCTTCCCGGGCC 3'
```

A 31 base "target" DNA (31mer) was also synthesized by the same method and had the following sequence:
5'TTTATTCACTGGCCGGCGGGGAATTCGTTTT 3'

M13mp7 single stranded phage DNA was prepared by the method of Sanger (*J. Mol. Biol.* (1980) 143, 161–178). The nucleotide sequence was confirmed by dideoxy sequencing. Digestion of the single stranded DNA by Eco RI or Bam HI was confirmed by agarose gel electrophoresis (Ricca, G. A., et al. *Proc. Natl. Acad Sci., U.S.A.* (1982) 79, 724–728).

Enzymes

T4 DNA ligase (lot no. 51131, 1.0 U/µL), T4 kinase (lot no. 66111, 10 U/µL) and the restriction endonuclease Bam HI (lot no. 46101, 10 U/µL) were purchase from Bethesda Research Labs (BRL).

Buffers and Other Reagents

Reaction buffer #3 (10×) is, after dilution to 1× concentration, 50 mM Tris-HCl (pH 8.0), 10 mM $MgCl_2$ and 100 mM NaCl TE (1×) is 100 mM Tris-HCl (pH 7.6) and EDTA. TES is 10 mM Tris HCl (ph 8.0), 1 mM EDTA and 400 mM NaCl SSSC is 750 mM NaCl, 50 mM $Na_3PO_4$ and 75 mM sodium citrate (pH 6.5). Kinase forward reaction buffer (5×) is 300 mM Tris-HCl (pH 7.8), 75 mM 2-mercaptoethanol, 50 mM $MgCl_2$ and 1.65 µM ATP. Sequenase™ buffer (5×) is, after dilution to 1 × concentration, 40 mM Tris-HCl (pH 7.5), 20 mM $MgCl_2$, and 50 mM NaCl. $\gamma$–$^{32}$P ATP (3000 Ci/mmol; 10 mCi/mL) was purchased from New England Nuclear Corp., Boston, Mass. Other buffers and methods not specifically detailed were as described by Maniatis, et al. "Molecular Cloning: A Laboratory Manual", (1982), Cold Spring Harbor Laboratory, Cold Spring Harbor, N.Y.

Digestion of M13mp7 with BamHI

A solution of 200 µL (1.1 µg/µL) of M13mp7 phage DNA, 16 µL (10 U/µL) of Bam HI and 24 µL of 10× reaction buffer #3 was incubated at 37° C. for 3 hours. Complete digestion was verified by 1% agarose gel electrophoresis. The solution was extracted with 240 µL of buffer equilibrated phenol and the aqueous phase was extracted twice with an equal volume, of a 24:1 mixture of chloroform and isoamyl alcohol. The resulting solution was treated with an equal volume of 5M $NH_4OAc$ and 2.5 volumes of absolute ethanol at 0° C. The well mixed solution was centrifuged for 40 min at 4° C. and the supernatant removed. The residue was washed with 70% ethanol and then dried at reduced pressure. The precipitate was diluted with 0.1 mM EDTA (pH=7.8) to a concentration of 1 w/t and µg/µL stored at −20° C.

Labeling of Reporter DNA

50 µL (1 pmol/µL) of the 124mer, 18 µL of 5× kinase buffer, 15 µL of $\gamma^{32}$P ATP and 7 µL (10 U/µL) of T4 kinase were incubated at 37° C. for 1.5 hours. The reaction solution was purified through a Nensorb column (DuPont) according to the manufacturer's instructions and solvent was removed under reduced pressure. The residue was dissolved in water to a concentration of 1 pmol/µL and stored at −20° C.

Target Specific Polymerization and Ligation of the DNAs

2 µL (0.5 pmol/µL) of Bam HI linearized M13mp7 DNA, 1 µL (1 pmol/µL) of labeled 124 mar, 1 µL (1 pmol/µL) of the 31met, 2 µL of 5× Sequenase™ buffer and 2 µL of water were heated to 80° C. for 5 min. and allowed to cool slowly to 23° C. After a brief spin to collect the liquid in the bottom of the tube, 1 µL of ATP (0.1M) and 1 unit of T4 DNA ligase, 10 units of Sequenase™ (a modified T7 DNA polymerase available commercially from United States Biochemical Corporation, Cleveland, Ohio) and dCTP to a final concentration of 133 µM were added to the reaction. The resulting solution was incubated at 23° C. for 12 hours. After this incubation, 10 units of Eco RI (1 µl) was added and the reaction was allowed to continue at 37° C. for an additional 1 hour.

Denaturing polyacrylamide gel electrophoresis of an aliquot from the above reaction showed a P labeled product of 138 bases in length. This product corresponds to the fill-in and ligation of the non-contiguously hybridized oligonucleotide 124mer and the Bam HI linearized M13mp7 up to the EcoRI site. The 138 base product is not observed in the absence of target 31mer (with target 31mer substituted by 1 µl of sterile deionized water). This demonstrates that the reaction is target specific and useful in accordance with the present invention.

In another example of this invention, again provided by way of illustration and not limitation, a single-stranded DNA oligomer was synthesized directly on a derivatized glass so as to provide a DNA whose 3' terminus was covalently attached to the modified glass surface. When phosphorylated with ATP and T4 polynucleotide kinase to give the 5' phosphate, this DNA-glass was reacted with T4 DNA ligase in the presence and absence of a target oligonucleotide to which a labeled reported oligonucleotide present in solution could non-contiguously bind. The results described below show that the presence of the target-oligonucleotide could be detected by the joining of two non-contiguously hybridized oligonucleotides.

MATERIALS AND METHODS

Preparation of Covalently Attached DNA on Glass
Controlled Pore Glass (CPG) (200/400 Mesh Size 96.2 nm dia-lot 08CO2—Electro-Nucleonics, Inc., Fairfield, N.J.) was dried and then reacted under inert atmosphere and anhydrous conditions with (1,2-epoxy-3-propylpropoxy) trimethoxysilane (Aldrich) according to the method of Jost, et al., *J. Chromatogr.*, 185 (1979), 403–412, and the references contained therein. The glass was washed extensively with dry ether and finally dried under vacuum at 100° C. for 4 hours. The glass was resuspended in absolute ethanol and a catalytic amount of $BF_3$ etherate (Aldrich) was added. The mixture was refluxed for 4 hours with stirring. The resulting white derivatized CPG was then washed extensively with absolute ethanol and dried under vacuum. The dried material was aliquoted into 1 µmole scale plastic DNA synthesis column assemblies (Biosearch Corp., San Rafael, Calif. product 8600-0456; approx. 50 mg/column).

DNA Synthesis

The derivatives CPG columns described above were used in the standard 1.0 mol phosphoramidate DNA synthesis protocol and reagents (Biosearch Corp.). The sequence synthesized on the glass was:
5'            CAATTAAGGAATGTATTAAGCTTGTG-TAATTGTTAA 3'

After deprotection of the synthesized DNA on the glass by treatment with concentrated $NH_4OH$ for 10 hours at 50° C., the glass was washed extensively and treated with ATP and T4 polynucleotide kinase (BRL) as described by the manufacturer to phosphorylate the 5' hydroxyl terminus. It should be noted that in the normal course of DNA synthesis on this instrument (the Biosearch 8650), the first nucleotide is supplied already attached to the controlled pore glass. The instrument thus assumes that the 3' A is already present on the glass. The actual sequence present on the glass then has one fewer A's at the 3' end than indicated above.

The 43 base "target DNA" had the sequence:
5'            GCTTAATACATTCCTTAATTGGGGC-CCGGGAAGAAAAAAAAAA 3'

The non-contiguously hybridizing reporter DNA (a 124mer) was as described in the previous example above. An additional 84mer DNA containing the same target hybridizing sequence portion (i.e., its 3' terminus) as the 124mer DNA was also used as a reporter molecule. The reporter DNAs were labeled with $\gamma^{32}P$ ATP and T4 kinase as described above in the previous example.

Hybridization and Ligation

In a presterilized 1.5 mL Sarstedt screw top tube, 10 µL of kinased DNA-glass suspension (approx. 50 pmoles), 200 fmoles of target (43mer) DNA, 5 µg of yeast tRNA (Sigma), and 400 fmoles of labeled reported DNA were combined with 5 µL of 5× ligase buffer (250 mM Tris HCl, pH=7.5, 50 mM $MgCl_2$, and 25% PEG) in a total volume of 18 µL. In the case of the negative controls (without tgarget molecules included) sterile deionized water was substituted for the 1 µL of target DNA solution. All reaction mixtures were heated to 95° C. for 5 min. and then slowly allowed to cool to room temperature (approx. 23° C.) over a period of 2½ hours. After cooling and a brief spin to collect the liquid in the bottom of the tube, 2 µL of dithiothreitol solution (0.1M), 3 µL of ATP 910 mM) and 2 µL of T4 DNA ligase (BRL or New England Biolabs), the reactions were incubated at 15° C. for 12 hours. Reactions were performed in duplicate.

Results

After extensive washing of the glass under native and DNA denaturing conditions, well established in the literature, the glass beads were counted in a Beckman LS 2800 scintillation counter to determine the retention of the $^{32}P$ labeled reported oligonucleotide. The following results were obtained:

| | cpm observed (Cerenkov) |
|---|---|
| +target | 22713 |
| | 22275 |
| −target | 595 |
| | 665 |
| empty tube | 123 |

These results show that the presence of a target DNA in a sample may be determined in accordance with the present invention.

Although the foregoing invention has been described in some detail by way of illustration and example for purposes of clarity of understanding, it will be obvious that certain changes and modifications may be practiced within the scope of the appended claims.

What is claimed is:

1. A kit for use in detecting a target polynucleotide sequence, which comprises in packaged combination:

a first polynucleotide complementary to and capable of hybridizing to a portion of a single strand of a target polynucleotide and having, or capable of having, means for immobilizing said first polynucleotide, a second polynucleotide, having, or capable of having, a label wherein said second polynucleotide is complementary to and capable of hybridizing to a portion of said single strand of said target polynucleotide other than and non-contiguous with the portion complementary to said first polynucleotide, and means for covalently attaching said first and second polynucleotides when said first and second polynucleotides are hybridized with said single strand of said target polynucleotide.

2. The kit of claim 1 wherein one of said first and said second polynucleotides is capable of undergoing an extension reaction in the presence of a polynucleotide polymerase and one or more deoxynucleoside triphosphates to become contiguous with the other of said first and said second polynucleotides when both first and second polynucleotides are hybridized to said single strand of said target polynucleotide, and said kit further comprises:

a polynucleotide polymerase, one or more deoxynucleoside triphosphates, and a ligase as a means for covalently attaching said first and second polynucleotides.

* * * * *